(12) United States Patent  (10) Patent No.: US 7,534,127 B2
Parker et al.  (45) Date of Patent: May 19, 2009

(54) IMPLANTABLE CONNECTOR (75) Inventors: John Parker, Roseville (AU); Ian Darley, Cromer Heights (AU); Dusan Milojevic, Westleigh (AU)

(73) Assignee: Cochlear Limited, Lane Cove (AU)

( * ) Notice: Subject to any disclaimer, the term of this patent is extended or adjusted under 35 U.S.C. 154(b) by 693 days.

(21) Appl. No.: 11/028,624

(22) Filed: Jan. 5, 2005

(65) Prior Publication Data
US 2005/0165464 A1    Jul. 28, 2005

(30) Foreign Application Priority Data
Jan. 5, 2004   (AU) .............................. 2004900013

(51) Int. Cl.
H01R 11/20     (2006.01)
(52) U.S. Cl. ...................................... 439/425; 439/909
(58) Field of Classification Search ................ 439/425, 439/426, 427, 444
See application file for complete search history.

(56) References Cited

U.S. PATENT DOCUMENTS

| 2,490,316 | A | * | 12/1949 | Ostrak | 403/340 |
| 2,858,518 | A | * | 10/1958 | Chrystie et al. | 439/426 |
| 3,784,959 | A | * | 1/1974 | Horton | 439/275 |
| 3,848,949 | A | * | 11/1974 | Falkner | 439/426 |
| 3,853,385 | A | * | 12/1974 | Palazzetti et al. | 439/190 |
| 4,023,882 | A | * | 5/1977 | Pettersson | 439/426 |
| 4,148,540 | A | * | 4/1979 | Hayes | 439/425 |
| 4,473,714 | A | * | 9/1984 | Brownell et al. | 174/78 |
| 4,495,917 | A | * | 1/1985 | Byers | 607/57 |
| 4,516,820 | A | * | 5/1985 | Kuzma | 439/289 |
| 4,532,930 | A | * | 8/1985 | Crosby et al. | 607/57 |
| 4,610,493 | A | * | 9/1986 | Masek | 439/98 |
| RE33,170  | E | * | 2/1990 | Byers | 607/57 |
| 5,105,811 | A | * | 4/1992 | Kuzma | 607/57 |
| 5,571,148 | A | * | 11/1996 | Loeb et al. | 607/57 |
| 5,782,645 | A | * | 7/1998 | Stobie et al. | 439/289 |
| 5,934,930 | A | * | 8/1999 | Camps et al. | 439/425 |
| 6,198,969 | B1 | * | 3/2001 | Kuzma | 607/37 |
| 6,321,126 | B1 | * | 11/2001 | Kuzma | 607/137 |
| 6,551,124 | B1 | * | 4/2003 | Gossmann | 439/411 |
| 6,654,643 | B1 | * | 11/2003 | Schmid | 607/116 |
| 7,054,691 | B1 | * | 5/2006 | Kuzma et al. | 607/57 |
| 7,225,028 | B2 | * | 5/2007 | Della Santina et al. | 607/57 |
| 7,303,422 | B2 | * | 12/2007 | Hoffer et al. | 439/359 |
| 7,347,751 | B2 | * | 3/2008 | Sweeney et al. | 607/119 |
| 2003/0167077 | A1 | * | 9/2003 | Blamey et al. | 607/57 |

* cited by examiner

*Primary Examiner*—Ross N Gushi
(74) *Attorney, Agent, or Firm*—Connolly Bove Lodge & Hutz LLP (57) ABSTRACT

An implantable electrical connector is disclosed for use with implanted medical devices. Each part of the connector has an array of contacts which can mate, one part being a cutting contact and the other half a receiving contact. When mated, this forms a reliable electrical connection.

36 Claims, 9 Drawing Sheets

FIG. 14b

IMPLANTABLE CONNECTOR

CROSS-REFERENCE TO RELATED APPLICATIONS

The present application claims priority from Australian Provisional Patent Application Number: 2004900013 filed on Jan. 5, 2004, the contents of which are incorporated herein by reference.

BACKGROUND

Field of the Invention

The present invention relates to an electrical connector for an implantable medical device.

Implantable medical devices include cardiac pacemakers, neurostimulators, cochlear implants, retinal prostheses, and many others. Frequently, there is a need to provide at least one electrical connection between various parts of an implantable medical device. For example, an implantable medical device for applying electrical stimulation could have an electrical connection between an implanted stimulator unit and a wire connected to an electrode element that applies stimulation to the desired region of tissue.

An electrical connection that is secure and reliable, ensures that the various components of the implantable medical device operate correctly, and that electrical current does not leak from the device and potentially cause damage to surrounding tissue.

In most implantable medical devices, the electrical connection is achieved via a permanent and rigid connection which cannot be readily disconnected and reconnected.

In the case of a cochlear implant, a stimulator unit embedded within the mastoid bone of the recipient, receives and directs stimulation signals to a plurality of electrodes that are inserted within the cochlea. Typically, the cochlear implant requires 22 to 24 electrical connections between the stimulator unit and the electrode array.

A hermetic feedthrough device normally provides the electrical connection between the wires connecting the electrodes to the stimulator unit. The wires connecting each of the electrodes are fixed to one side of the hermetic feedthrough device to form an electrical connection with the implant circuitry, which is connected to the other side of the feedthrough device. However, such an electrical connection does not allow for ready disconnection of the wires from the stimulator unit for later reconnection.

Hence, it has not been possible to replace the stimulator unit of a cochlear implant without replacing the entire cochlear implant. The electrode array is inserted within the cochlea, and removal requires the array to be removed from the position it has been in for some time, potentially years. This is problematic because of the risk of causing damage to the sensitive tissue structure.

The provision of a connector for an implantable device such as a cochlear implant Must be able to be used in a very confined space, since the components normally have dimensions in the order of nanometers or microns, up to the mm scale.

To further complicate the provision of such a connector system, the reconnection process must be able to take place in a fluid environment. This is desirable because a part of the system, for example the electrode array, can preferably remain permanently in position within the body.

It is desired to provide an implantable connector system capable of providing repeatable connections between a plurality of conductors of an implantable medical device.

SUMMARY

In accordance with one aspect of the present invention, there is provided an implantable electrical connector comprising:
a first body portion having a plurality of exposed contacts; and
a second body portion having a plurality of contacts being spatially alignable with said plurality of contacts of said first body portion;
wherein each individual pair of corresponding contacts comprises a cutting contact and a receiving contact, to enable releasable inter-engagement therebetween, upon alignment of, and compression between, said first and second body portions.

BRIEF DESCRIPTION OF THE DRAWINGS

The present invention will now be described in relation to a number of examples, with reference to the accompanying drawings, in which.

DETAILED DESCRIPTION

Figure 1:
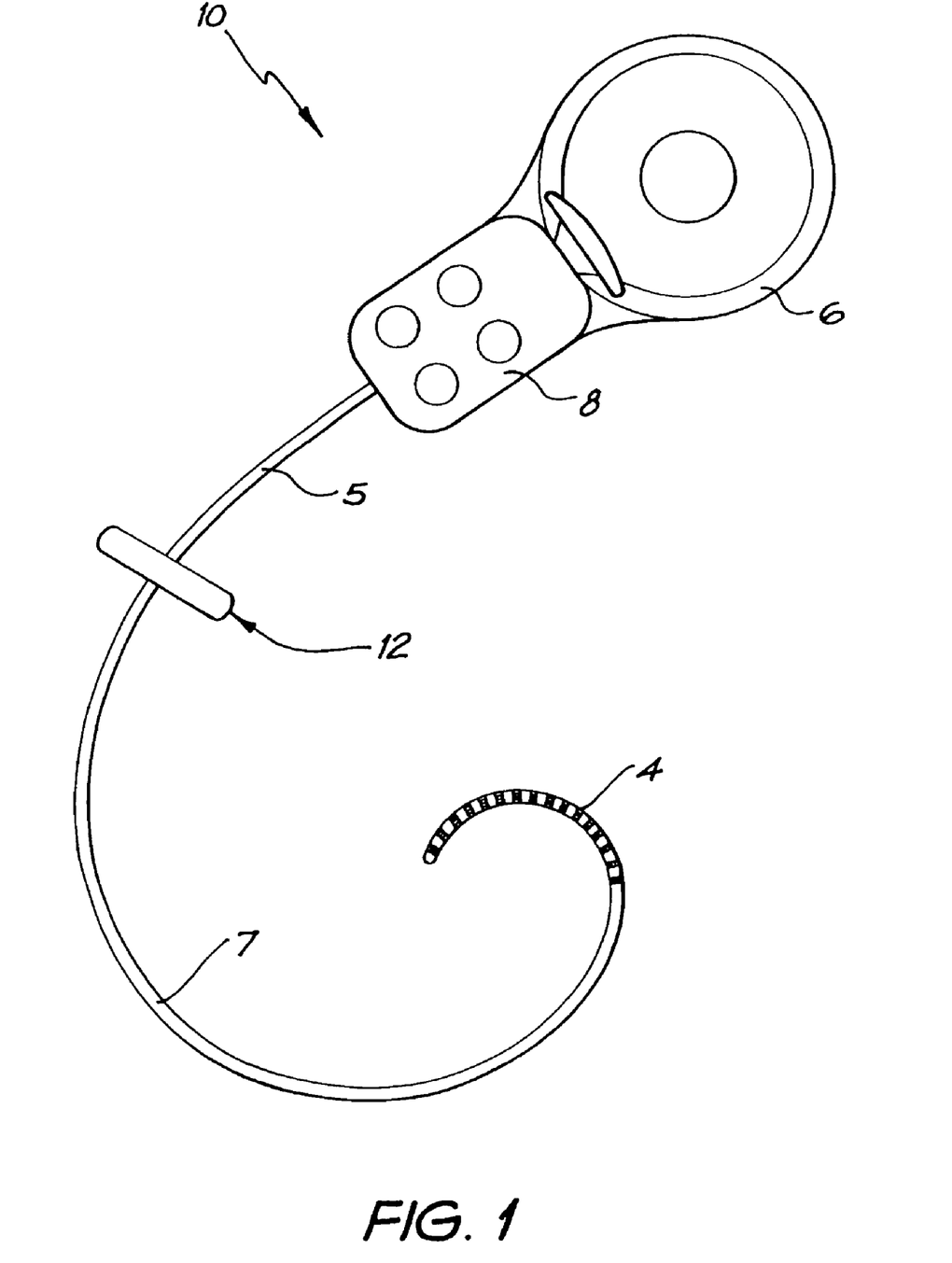
FIG. 1 shows a cochlear implant package having an implantable connector.

Referring to FIG. 1, an implantable cochlear implant device 10 includes a multi-connector contact connector 12, an implanted stimulator unit 8, a receiver/transmitter coil 6 and an electrode array 4.

The implanted stimulator unit 8 hermetically houses electronic circuitry required for its operation. The receiver/transmitter coil 6 is capable of receiving a coded signal from an external speech processor (not shown) for processing and decoding by the electronic circuitry to form a stimulation signal. The stimulation signal can be applied to the electrode array 4, which is disposed within the cochlea proximal to the auditory nerves of the recipient.

The stimulator unit 8 is electrically connected to the electrode array 4, via each of a cable 5, the connector 12 and a cable 7. The cables 5, 7 each include a plurality of wires, the number of which generally conforms to the number of electrodes on the electrode array 4. In this arrangement, the electronic circuitry is able to select a particular electrode of the electrode array 4 to provide stimulation to a desired region of the cochlea.

The connector 12 provides a releasable electrical connection between respective wires in cables 5 and 7. This enables the stimulator unit 8 to be removed and replaced, without disturbing the electrode array 4 from within the cochlea. The connector 12 is reusable so that if a stimulator unit 8 requires replacement, a reconnection can be readily re-established between the new cable 5 and the existing electrode array 4.

Figure 2:
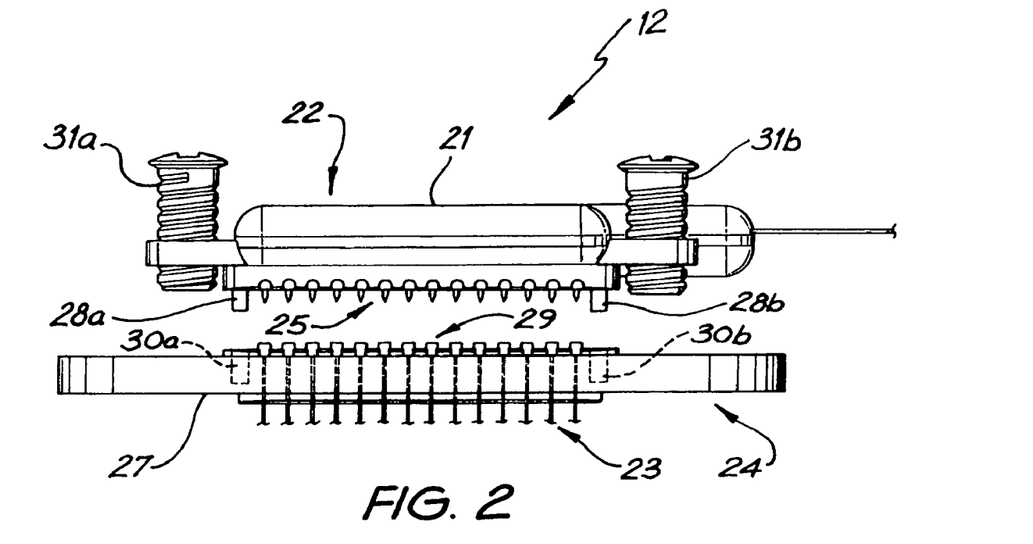
FIG. 2 is a side view of the connector of FIG. 1.
Figure 3:
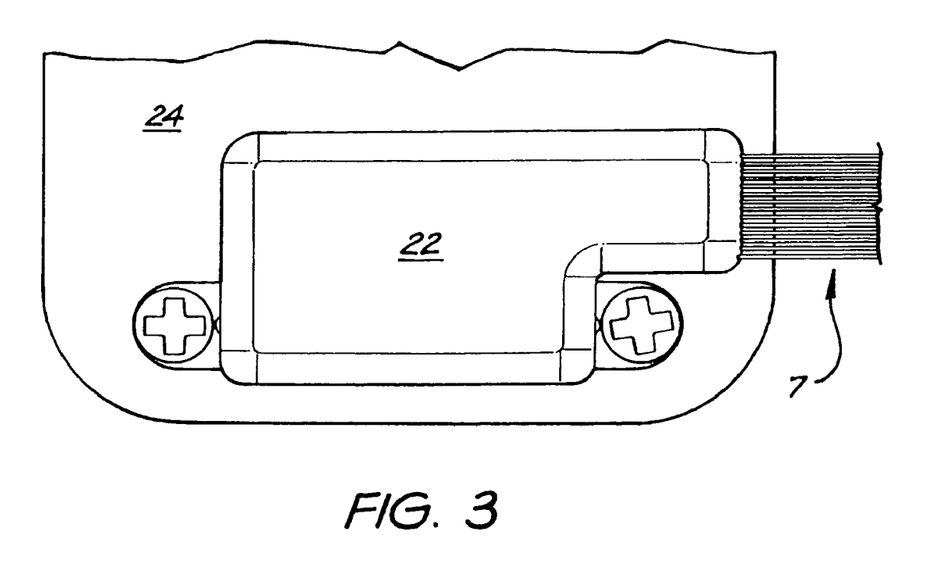
FIG. 3 is a top view of the connector of FIG. 1.

Referring now to FIG. 2, the connector 12 includes a first body portion 22 and a second body portion 24. The first body portion 22 is permanently connected to wires in the cable 7 leading to the electrode array 4 and the second body portion 24 is permanently connected to the wires of cable 5 leading to the stimulator unit 8.

The first body portion 22 provides an insulating element 21 supporting each of a plurality of linearly arranged, exposed, cutting electrical contacts 25.

Figure 4:
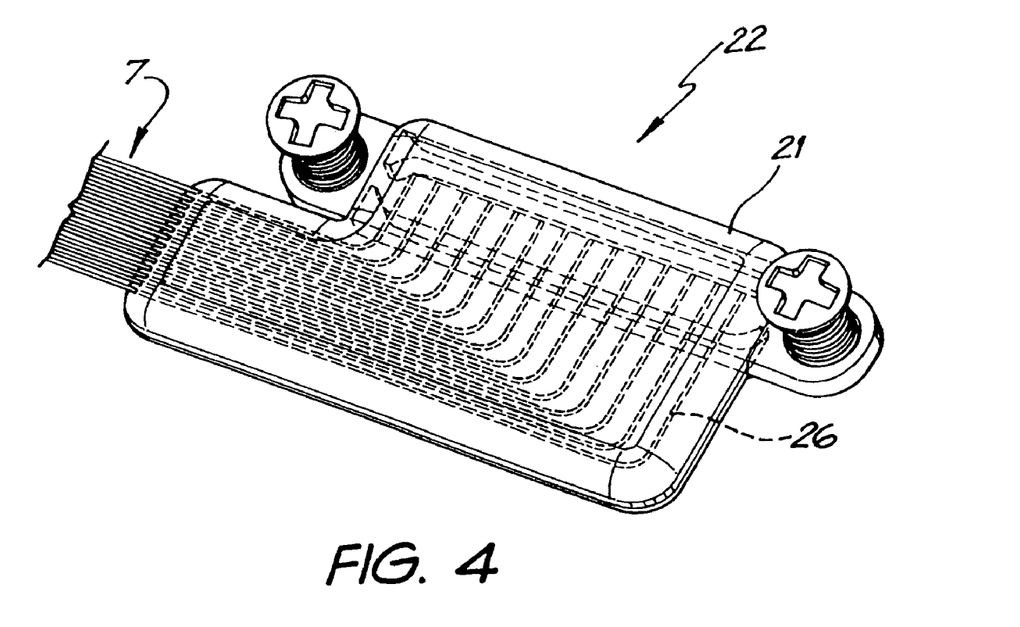
FIG. 4 is a perspective view of a first body portion of the connector of FIG. 1, with conductive wires shown in phantom.

Referring to FIGS. 2 and 4, each cutting contact 25 is connected to a corresponding wire 26 that extends through, and is encapsulated by, the insulating element 21. Each encapsulated wire 26 terminates at an external connection point of the first body portion 22, where each wire 26 is permanently spot welded or crimped, to a corresponding wire in the cable 7.

Figure 6:
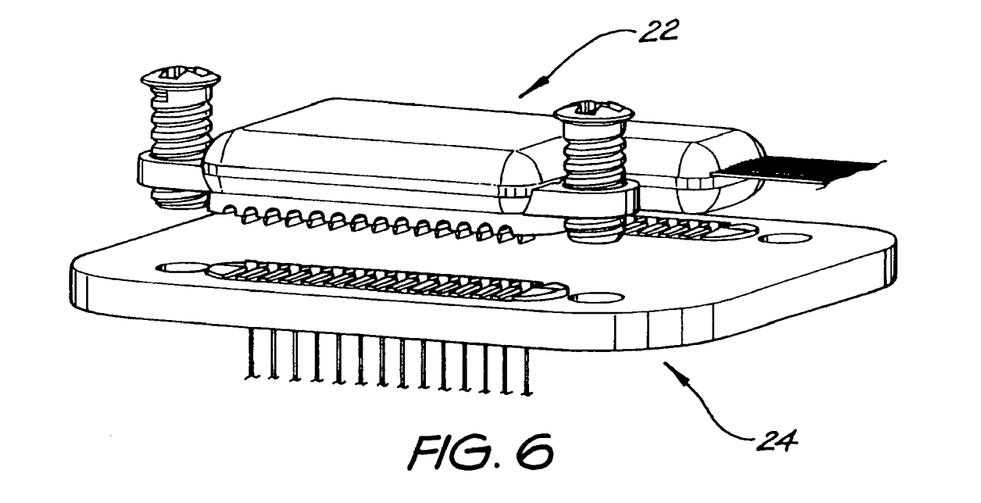
FIG. 6 is another perspective view of the connector of FIG. 1.

Similarly, the second body portion 24 provides an insulating element 27 supporting each of a plurality of linearly arranged, exposed, receiving electrical contacts 29. As shown in FIGS. 2 and 6, each receiving contact 29 is connected to a corresponding wire 23 extending from an inner face to an outer face of the insulating element 27.

As with the first body portion 22, each of the wires 23 are connected at the outer face of the second body portion 24, to conductive wires 23 in the cable 5. This connection can be made using spot welding or crimping.

Preferably, the exposed contacts 25, 29 extend to or beyond the surface of the respective insulator elements 21, 27.

The first body portion 22 and the second body portion 24 can be manufactured in accordance with the method described in the present Applicant's co-pending patent application, International Patent Application No. PCT/AU03/012888, which is incorporated herein by reference. This application describes a method of forming an electrically conducting feedthrough device, and as such the same principle can be employed to form the insulator elements 21, 27 with the contacts 25, 29 encapsulated therein and extending therethrough. In this way, a continuous length of wire can be used for each of the cable conductors and the encapsulated wires. Hence, spot welding or crimping is not required at the external connection points of each of the body portions.

Figure 5:
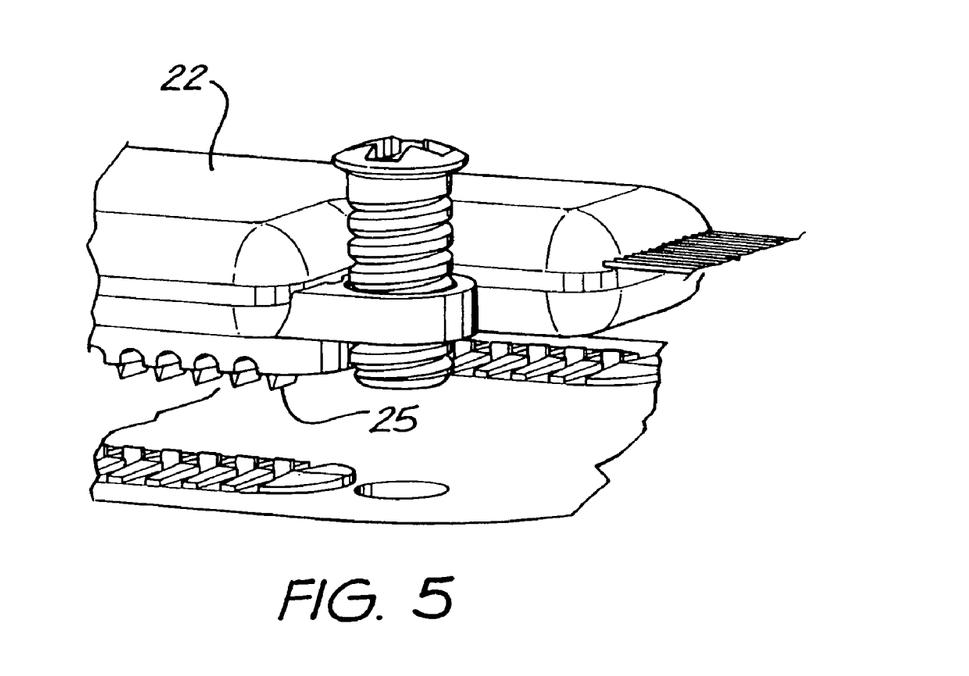
FIG. 5 is a perspective detail of a securing mechanism used in the connector of FIG. 1.

The first body portion 22 can be provided with a pair of lugs 28a and 28b, each configured to engage with a corresponding pair of recesses 30a, 30b in the second body portion 24. The lugs 28a, 28b and the corresponding recesses 30a, 30b form an alignment means to help align the contacts 25, 29 and the first and second body portions 22, 24 The first body portion 22 is further provided with a pair of screws 31a, 31b which can be received in a threaded recess in either the first or second body portions. The screws and the threaded recesses together form an engaging means to maintain the first body portion 22 and the second body portion 24 in secure engagement to ensure that reliable electrical contact is maintained between the respective contacts 25, 29.

If the stimulator unit 8 requires replacement, the screws can be removed from the connector 12 to allow the second body portion 24 to be removed away from the first body portion 22. A replacement stimulator unit 8 having a second body portion 24 of the connector element 12 configured to conform with the existing first body portion 22 can then be positioned to complete connection from the stimulator unit to the existing electrodes of the existing electrode array. The connector 12 can be reassembled by screwing together the new second body portion 24 with the existing first body portion 22. As the dimensions of the first and second body portions 22 and 24 are manufactured in an identical manner, alignment of the respective contacts 25, 29 is readily achieved.

While the above example uses separate alignment means and engaging means, it should be appreciated that these could be combined, such that the engagement means, in the action of engaging the first body portion 22 to the second body portion 24, also aligns each of the respective contacts 25 and 29.

The method of achieving a releasable electrical connection between the contacts 25, 29 of the first and second body portions 22, 24 will now be described in further detail with reference to FIGS. 8a to 8c.

Figure 8A:
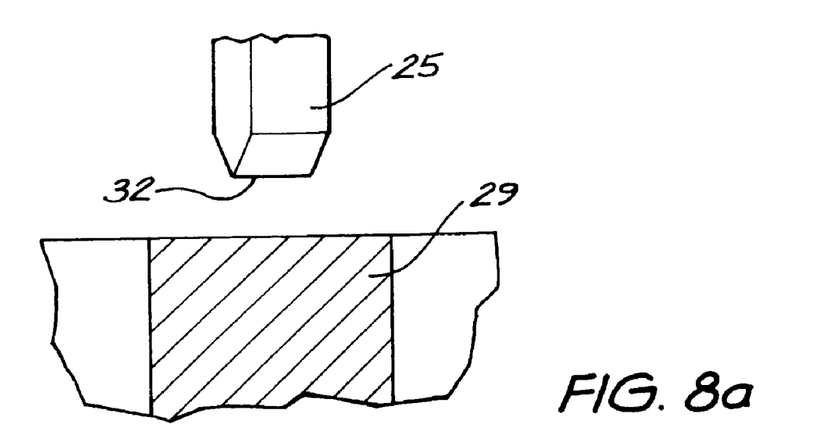
FIGS. 8a to 8c schematically show an electrical connection between contact pairs of the connector of FIG. 1.

FIG. 8a shows a single pair of contacts 25, 29, in which cutting contact 25 on the first body portion is formed to be able to deform and/or penetrate the receiving contact 29 on the second body portion, to thereby provide a path for electrical conduction through the connector 12.

The cutting contact 25 is of increased hardness than the receiving contact 29 and this enables the penetration and/or deformity of the softer receiving contact 29 to occur. This difference in hardness can be achieved by the choice of material used for each of the contacts 25, 29. For example, the cutting contact 25 can be made from iridium which has greater hardness properties than platinum, which can be used for receiving contact 29. It is envisaged that the same base material may be used for each of the contacts 25, 29, but cutting contact 25 can be treated to improve its hardness characteristics or contact 29 can be treated to increase softness. Treatments such as alloying and annealing, respectively can be used to achieve this. (alloying will increase hardness, e.g. by adding iridium to platinum.

Alternatively or additionally, the receiving contact 29 can be provided with a sharpened edge 32 to assist in breaking the surface of the receiving contact 29. The sharpened edge 32 can be achieved through electrochemical sharpening or other similar methods known in the art.

Figure 8B:
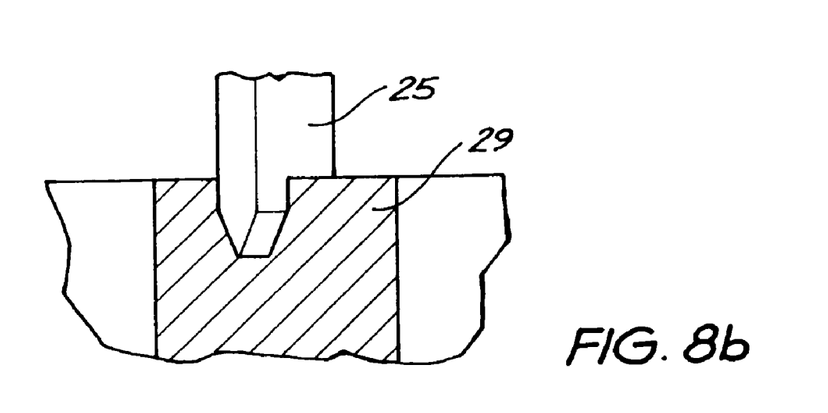
Figure 8C:
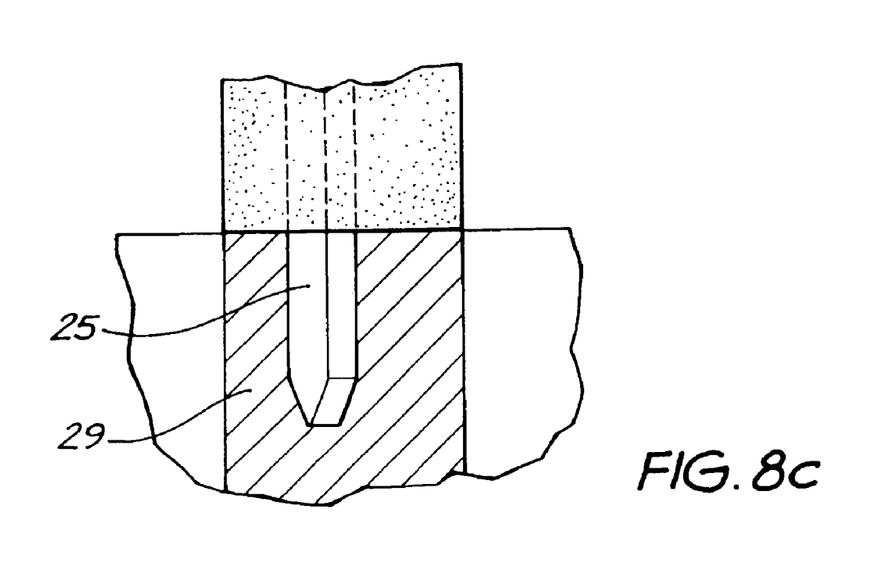

During connection of the connector element 12, as the first and second body portions 22, 24 of the connector are compressed together, each of the corresponding contacts 25, 29 are brought into contact with one another in the manner as depicted in FIGS. 8a to 8c. The cutting contact 25 penetrates the receiving contact 29 as the first and second body portions 22, 24 are securingly engaged together. As shown in FIG. 8c, the cutting contact 25 is securely maintained in electrical contact with the receiving contact 29.

As both the cutting contact 25 and the receiving contact 29 are encapsulated within an insulating material, the connection is electrically isolated. Such a connection occurs between each of the corresponding contacts 25, 29, thereby providing an electrical conductive path from a lead or wire extending from the stimulator unit through the connector 12 to the corresponding lead or wire connected to an electrode of the electrode array.

The number of connections can vary dependant upon the number of wires and electrodes used by the system, but can typically vary between 16 and 32. Each of the conductors of the connector 12 can be arranged in multiple rows rather than a single row.

Figure 9A:
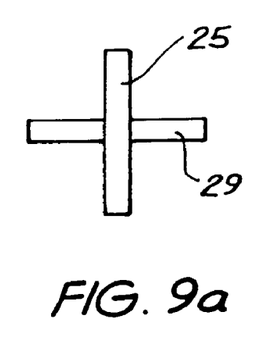
FIGS. 9a to 9c show top views of alternative arrangements of contact pairs.
Figure 9B:
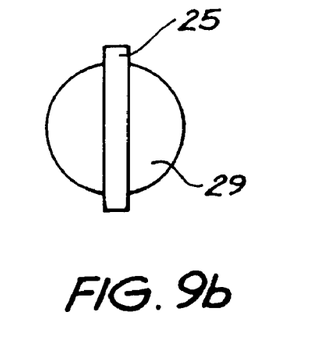
Figure 9C:
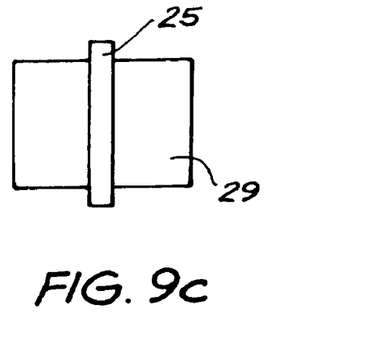

Whilst the contacts 25, 29 are shown in FIGS. 8a to 8c, as being substantially rectangular in cross-section, other shapes such as square or circular are also envisaged and are shown from a top view in FIGS. 9a to 9c.

As can be appreciated in FIGS. 9a to 9c, due to the penetrative nature of the electrical connection between each of the contacts 25, 29, the connector can be designed allowing a relative degree of tolerance between the positions of each of the corresponding pairs of contacts.

Figure 10A:
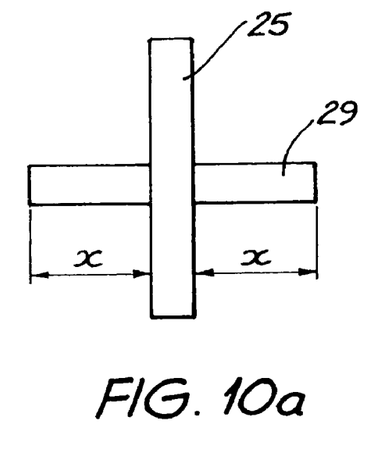
FIGS. 10a and 10b each show a top view of the connector of FIG. 1, depicting the tolerance that is provided in the electrical connection.
Figure 10B:
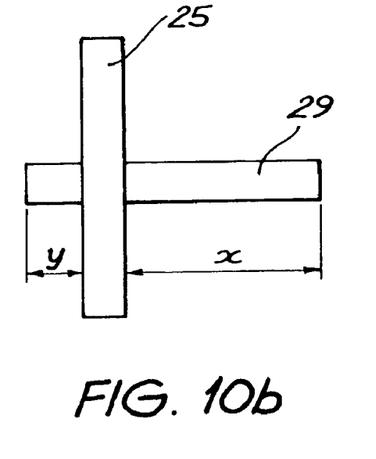

As shown in FIGS. 10a and 10b, the cutting contact 25 merely needs to penetrate the corresponding contact somewhere along its length, not necessarily in the middle of the contact to enable effective electrical connection to occur.

Figure 7:
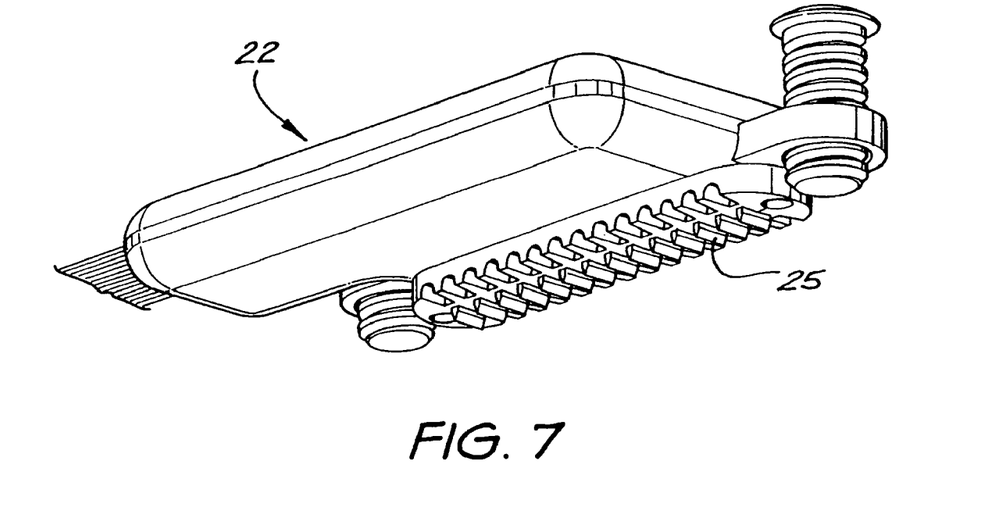
FIG. 7 is a perspective view of the first body portion of the connector of FIG. 1.

A layer of silicone can be provided around the base of each of the contacts 25, 29. The surface of the receiving contact 29 can be covered with silicone as shown in FIGS. 13b and 13c. This assists in preventing body fluid entering the area of electrical connection and providing an area of insulation. Further, the receiving contact 29 can be sprayed with a thin layer of parylene. Parylene not only has the ability to increase the mechanical strength of fine metallic structures but also acts as an efficient electrical insulator. The cutting contact 25 (of FIGS. 6-8) can penetrate through the layer of silicone and/or parylene and into the receiving contact 29 to enable electrical connection to be achieved.

Figure 11A:
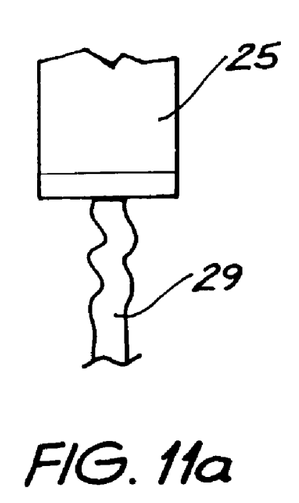
FIGS. 11a and 11b are side views of the contacts depicting problems that can occur during the connecting motion.
Figure 11B:
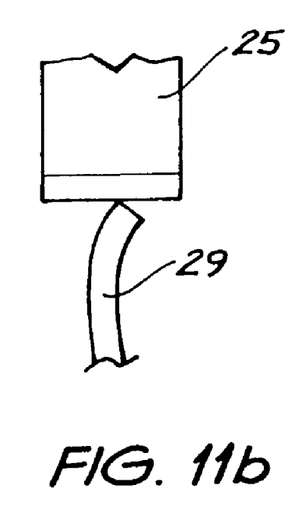

As well as providing efficient sealing between the contact of the first and second body portions 22, 24, this arrangement provides support to the contacts 25, 29 during the connecting action. In action, in the absence of a layer of silicone or parylene, as the cutting contact 25 is brought towards the receiving contact 29, the receiving contact 29 may collapse or bend upon contact, thereby greatly affecting the integrity of the electrical connection. This is shown diagrammatically in FIGS. 11a and 11b. FIG. 11a shows the receiving contact 29 collapsing and FIG. 11b. shows the receiving contact 29 bending, upon contact with the cutting contact 25.

Figure 12A:
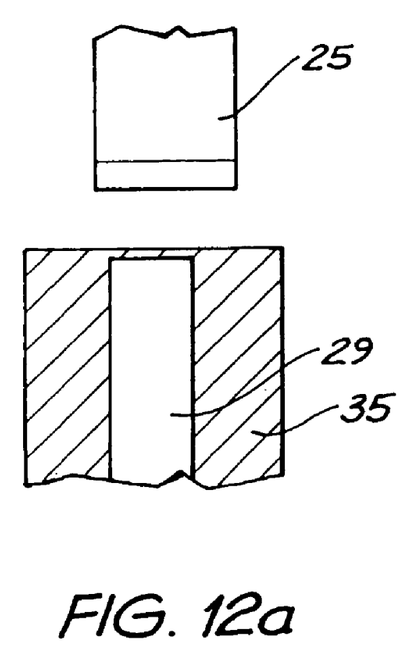
FIGS. 12a to 12b show side views of an alternative arrangement, in which the contacts are supported to facilitate penetration.
Figure 12B:
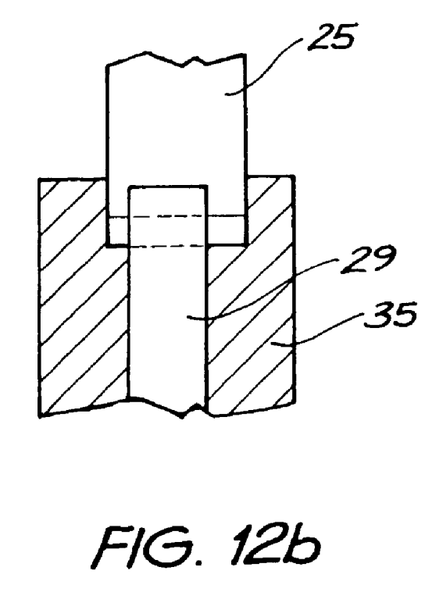

As shown in FIGS. 12a and 12b, the provision of a layer of silicone 35 around the receiving contact 29 can support the receiving contact 29 sufficiently to enable penetration by the cutting contact 25. As shown in FIG. 10b, the cutting contact 25 is able to slice through the silicone coating 35 to penetrate receiving contact 29, thereby allowing an electrical path to form. The silicone layer around the receiving contact 29 not only provides sufficient support to enable penetration, but also provides a resilient compressing action on the receiving contact 29 to stay in close proximity of the cutting contact 25. The space where contacts 25, 29 are positioned is confined and the silicone, in one application, fills that cavity. As cutting contact 25 slices through and splits receiving contact 29, the silicone elastomer can help to keep two sections of receiving contact 29 in close contact with the cutting contact 25 as shown for example in FIGS. 14a and 14b.

Figure 13A:
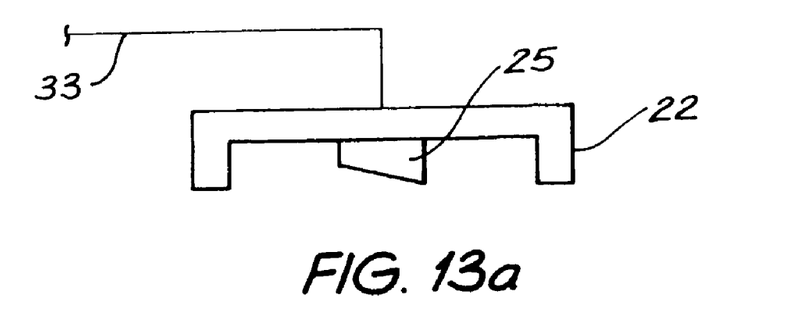
FIGS. 13a to 13c show side section views of an alternative arrangement of the contact pairs.
Figure 13B:
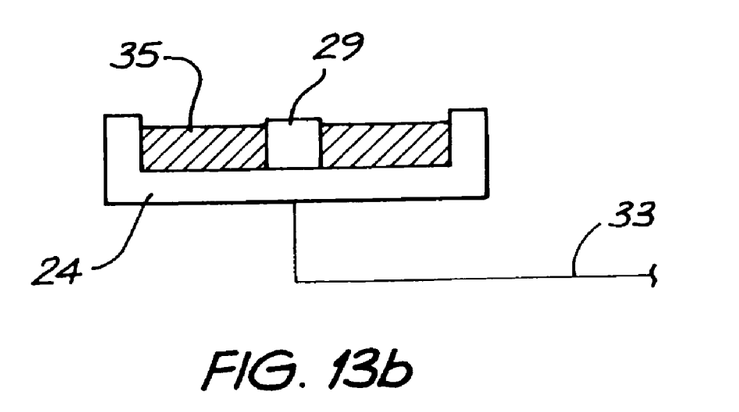
Figure 13C:
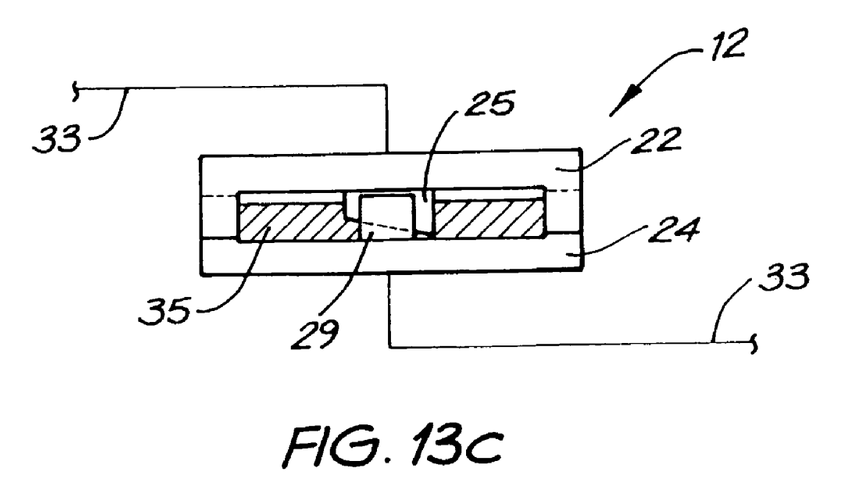

A connector 12 employing this arrangement is shown in more detail in FIGS. 13a and 13b. These figures depict a sectioned end view of the connector 12, and show the connection of one of the corresponding pairs of contacts 25, 29 As earlier described, the cutting contacts 25 are harder than the receiving contacts 29. Further, the cutting contacts can be sharpened to assist penetration into the receiving contact 29. A layer of silicone 35 is then provided over the receiving contact 29, as described above. Upon bringing the first body portion into alignment and contact with the second body portion, each cutting contact 25 penetrates a corresponding receiving contact 29. The surrounding silicone layer 35 provides an efficiently sealed electrical connection through the connector 12.

The shape of the cutting contact 25 can take a number of forms to aid in penetrating the receiving contact 29 and surrounding silicone. In the example shown in FIG. 13a, the cutting contact 25 is angled to represent a blade. However, the cutting contact 25 could be shaped in a number of alternative ways and still achieve the same result.

In use, it is preferable that the first body portion 22, which includes the contacts 25 extending therefrom, is connected to the part of the implantable system which is intended to remain permanently in place. In relation to the cochlear implant application shown in FIG. 1, the first body portion 22 is connected to the electrode array 7, which is intended to remain in place within the cochlea of the recipient throughout the life of the recipient. The second body portion 24 of the connector 12 is connected to the stimulator unit 8, which may require replacement or upgrading over the lifetime of the recipient. Therefore, as the permanent portion of the connector 12 includes the cutting contact 25, a replacement Stimulator unit 8 having a matching connector body portion with contacts 29 capable of being penetrated by the contacts 25, can easily be implanted within the recipient and electrically connected to the permanently positioned electrode array. This ensures that a reliable electrical connection is possible each time a non-permanent aspect of the implantable system requires replacement.

Turning to FIGS. 12a and 12b there is shown an alternative arrangement in which there is a sharpened insulator having a conductive surface exposed Leakage of body fluids is further impaired as conductive surfaces are positioned deeper into the structure. The sharpness of the contact can be adjusted as needed during design or fabrication. The silicone elastomer layer around the contact not only provides support to enable penetration but also provides a compressing action on the receiving contact 29 to stay in close proximity of the cutting contact 25.

Figure 14A:
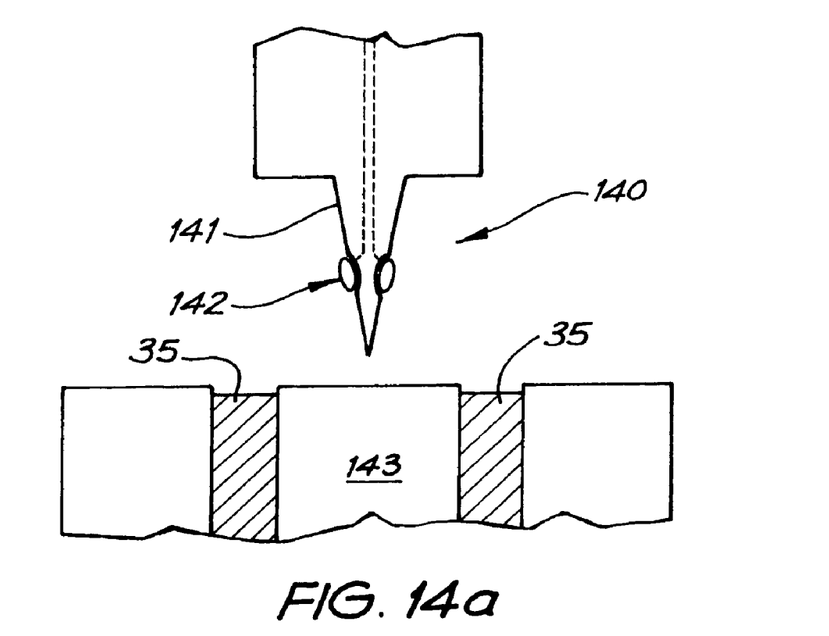
FIGS. 14a and 14b show yet a further alternative arrangement of the contact pairs.
Figure 14B:
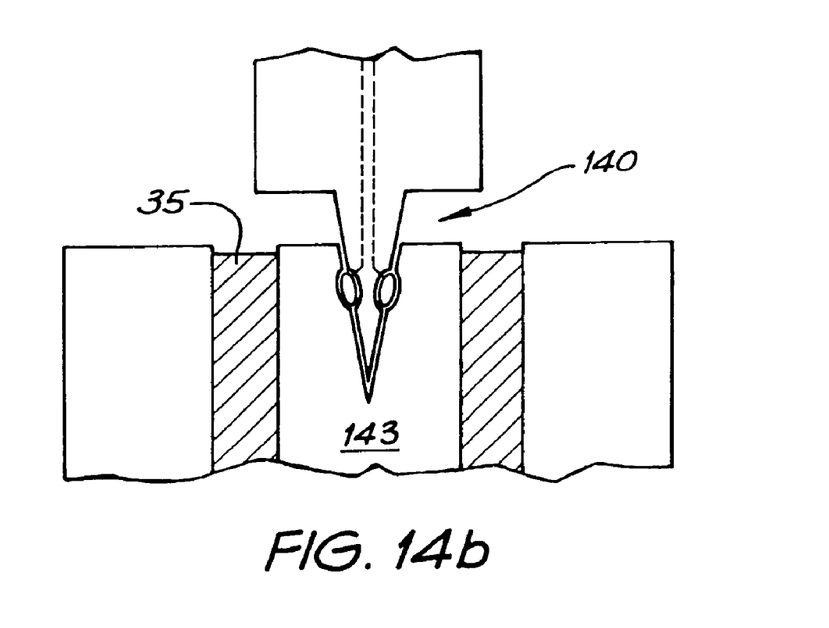

FIGS. 14a and 14b show an alternative arrangement where the cutting action and the conducting action are separated. The cutting contact 140 is wedge-shaped and includes a non-conductive ceramic portion 141 and a conductive portion 142. The ceramic portion 141 which performs the cutting, also houses the conductive portion 142 which is arranged with a externally exposed contact surface to make contact with the receiving contact 143.

In one example, the conductive portion 142 is platinum, although iridium can also be used. The silicone 35 provides a spring action that keeps the split halves of the receiving contact 143 in close contact with the cutting contact 140.

While the example described in relation to FIG. 1 provides a connector 12 as a separate unit remote from the housing of the implanted stimulator unit 8, the connector 12 can also be incorporated into the housing of the stimulator unit 8. The first or second body portion 22, 24 of the connector 12 can be formed on the surface of the stimulator unit 8, and connection would occur by securing the existing body portion in place. Other variations of the positioning of the body portions of the connector 12 could also be envisaged.

The connector just described provides one-to-one connection, in a matching pattern between two adjoining surfaces. An advantage of the connector device is that a part of the device can be electrically disconnected from another part of the implanted device without the need to remove the entire device.

It will be understood that the layout and geometry of the connector shown can readily be varied as required depending upon the requirements of the connection. It could be configured in a more radial arrangement, for example, with suitable modifications to the retaining structures. However, the relatively linear arrangement shown is preferred.

Further, the connector can enable multiple connection/disconnection of parts of the implanted device without affecting the functionality of the device.

Such a connector allows greater design flexibility of implantable medical devices requiring multiple electrical connections between parts, and enables such devices to be upgraded or replaced without the need to remove those elements of the device which are fixed or secured in place.

Whilst the present invention has been described in relation to a specific application to implantable medical devices, in particular cochlear implants, it should be appreciated that the application of the present invention is not confined to medical applications. For example, in the electronics field there are a variety of applications of the present invention where it is necessary to make a connection or connections between components of an electronics assembly.

What is claimed is:

1. An implantable electrical connector comprising:
a first body portion having a plurality of first contacts;
a second body portion having a plurality of second contacts, wherein said first and second body portions are configured such that each said second contact is operatively aligned with a corresponding first contact when the first and second body portions are engaged with each other;
wherein each individual pair of corresponding first and second contacts comprises a penetrating contact and a receiving contact, said penetrating and receiving contacts configured to releasably inter-engage therebetween upon engagement between said first and second body portions,
and further wherein at least one of said first or second contacts is exposed to the environment prior to their engagement; and
a non-penetrating conducting portion disposed on said penetrating contact, wherein said penetrating contact is non-conducting.

2. The implantable connector of claim 1, wherein said first contacts are said penetrating contacts configured to at least partially penetrate said receiving contacts, and wherein and said second contacts are said receiving contacts configured to receive said penetrating contacts.

3. The implantable connector of claim 1, wherein said penetrating contacts are formed from a harder material than said receiving contacts.

4. The implantable connector of claim 1, wherein said receiving contacts are substantially surrounded by a resilient material.

5. The implantable connector of claim 1, wherein each of said penetrating contacts are sharpened to facilitate penetration into the corresponding receiving contact.

6. The implantable connector of claim 1, further comprising a silicone layer disposed over a portion of either said first or said second contacts.

7. The implantable connector of claim 1, further comprising a polyxylylene polymers layer disposed on either said first or said second contacts and configured to provide additional mechanical strength and electrical insulation.

8. The implantable connector of claim 1, further comprising an engagement element on at least one of said first and second body configured to retain the forced engagement between said first and second body portions.

9. The implantable connector of claim 1, further comprising an alignment element on at least one of said first and second body configured to align said first and second body portions prior to said forced engagement.

10. The implantable connector of claim 1, wherein said non-conducting penetrating contact comprises ceramic.

11. The implantable connector of claim 1, wherein each of the first and second contacts are made from a metal.

12. The implantable connector of claim 11, wherein said penetrating contacts are made from iridium.

13. The implantable connector of claim 12, wherein said receiving contacts are made from platinum.

14. An implantable hearing prosthesis, comprising:
a first component electrically connected to a first connector portion having a plurality of first contacts; and
a second component electrically connected to a second connector portion having a plurality of second contacts, wherein said first and second body portions are configured such that each said second contact is operatively aligned with a corresponding first contact when the first and second body portions are engaged with each other;
wherein each individual pair of corresponding first and second contacts comprise a penetrating contact and a receiving contact, said penetrating and receiving contacts configured to realeasably inter-engage therebetween upon engagement between said first and second components,
and further wherein at least one of said first or second contacts are exposed to the environment prior to their forced engagement.

15. The hearing prosthesis of claim 14, wherein said first contacts are said penetrating contacts and said second contacts are said receiving contacts.

16. The implantable hearing prosthesis of claim 14, wherein said penetrating contacts are formed from a harder material than said receiving contacts.

17. The implantable hearing prosthesis of claim 14, wherein said receiving contacts are substantially surrounded by a resilient material.

18. The implantable hearing prosthesis of claim 14, wherein some or all of said penetrating contacts are sharpened to facilitate penetration into the corresponding receiving contact.

19. The implantable hearing prosthesis of claim 14, wherein each of the first and second contacts are made from a metal.

20. The implantable hearing prosthesis of claim 19, wherein said penetrating contacts are made from iridium.

21. The implantable hearing prosthesis of claim 20, wherein said receiving contacts are made from platinum.

22. The implantable hearing prosthesis of claim 14, wherein the implantable hearing prosthesis is a cochlear implant.

23. The implantable hearing prosthesis of claim 22, wherein the first component is a stimulator unit, and the second component is an electrode array.

24. The implantable hearing prosthesis of claim 23, wherein the second contacts are the receiving contacts.

25. The implantable hearing prosthesis of claim 24, wherein the second connector portion is attached to or part of the second component.

26. A cochlear implant, comprising:
a first component electrically connected to a first connector portion having a plurality of first contacts; and
a second component electrically connected to a second connector portion having a plurality of second contacts, the second contacts being operatively alignable with corresponding ones of said first contacts;

wherein each individual pair of corresponding first and second contacts comprises a cutting contact and a receiving contact, to enable releasable inter-engagement and electrical connection therebetween, upon alignment of and forced engagement between said first and second connector components.

27. The cochlear implant of claim 26, wherein said first contacts are said penetrating contacts and said second contacts are said receiving contacts.

28. The cochlear implant of claim 26, wherein said penetrating contacts are formed from a harder material than said receiving contacts.

29. The cochlear implant of claim 26, wherein said receiving contacts are substantially surrounded by a resilient material.

30. The cochlear implant of claim 26, wherein some or all of said penetrating contacts are sharpened to facilitate penetration into the corresponding receiving contact.

31. The cochlear implant of claim 26, wherein each of the first and second contacts are made from a metal.

32. The cochlear implant of claim 31, wherein said penetrating contacts are made from iridium.

33. The cochlear implant of claim 32, wherein said receiving contacts are made from platinum.

34. The cochlear implant of claim 26, wherein the first component is a stimulator unit, and the second component is an electrode array.

35. The cochlear implant of claim 34, wherein the second contacts are the receiving contacts.

36. The cochlear implant of claim 35, wherein the second connector portion is attached to or part of the second component.

* * * * *